US008835477B2

(12) United States Patent
Erdelmeier et al.

(10) Patent No.: US 8,835,477 B2
(45) Date of Patent: Sep. 16, 2014

(54) METHOD FOR THE SYNTHESIS OF 2-THIOHISTIDINE AND THE LIKE

(75) Inventors: Irène Erdelmeier, Paris (FR); Sylvain Daunay, Nogent sur Marne (FR)

(73) Assignee: Tetrahedron, Vincennes (FR)

( * ) Notice: Subject to any disclaimer, the term of this patent is extended or adjusted under 35 U.S.C. 154(b) by 12 days.

(21) Appl. No.: 13/500,887

(22) PCT Filed: Oct. 6, 2010

(86) PCT No.: PCT/EP2010/064947
§ 371 (c)(1),
(2), (4) Date: Aug. 30, 2012

(87) PCT Pub. No.: WO2011/042478
PCT Pub. Date: Apr. 14, 2011

(65) Prior Publication Data
US 2012/0330029 A1 Dec. 27, 2012

(30) Foreign Application Priority Data

Oct. 6, 2009 (FR) ..................................... 09 56968

(51) Int. Cl.
*A61K 31/417* (2006.01)
*C07D 233/42* (2006.01)
*C07D 233/84* (2006.01)

(52) U.S. Cl.
CPC .................................. *C07D 233/84* (2013.01)
USPC ........................................ 514/386; 548/316.4

(58) Field of Classification Search
USPC ........................................ 548/316.4; 514/386
See application file for complete search history.

(56) References Cited

U.S. PATENT DOCUMENTS

| 2009/0093642 A1 | 4/2009 | Trampota |
| 2012/0136159 A1 | 5/2012 | Erdelmeier |

FOREIGN PATENT DOCUMENTS

| WO | WO 95/00494 | 1/1995 |
| WO | WO 95/18108 | 7/1995 |
| WO | WO-2011/042480 | 4/2011 |

OTHER PUBLICATIONS

Ito, S., "Synthesis of 2-5-cysteinylhistidine and 2-mercaptohistidine via bromolactone derivative of histidine", Journal of Organic Chemistry, vol. 50, No. 19, (1985), pp. 3636-3638.*

Ishikawa, Y. et al. Journal Biological Chemistry, 1974, vol. 249 (14), pp. 4420-4427.*
Erdelmeier, Irene, et al.; "Cysteine as a sustainable sulfur reagent for the protecting-group-free synthesis of sulfur-containing amino acids: biomimetic synthesis of $_L$-ergothioneine in water;" The Royal Society of Chemistry 2012, Jun. 20, 2012 on http://pubs.rsc.org DOI:10.1039/c2gc35367a; www.rsc.org/greenchem; 10 pages.
Ito, S., "Synthesis of 2-5-cysteinylhistidine and 2-mercaptohistidine via bromolactone derivative of histidine", Journal of Organic Chemistry, vol. 50, No. 19, Sep. 1985, pp. 3636-3638, XP009129621, DOI: 10.1021/jo00219a044.
Ishikawa, Y. et al., "Participation of an intermediate sulfoxide in the enzymatic thiolation of the imidazole ring of hercynine to form ergothioneine," The Journal of Biological Chemistry, Jul. 25, 1974, vol. 249, No. 14, pp. 4420-4427, XP002568730, ISSN: 0021-9258.
Xu, J. et al., "Synthesis of L-(+)-ergothioneine," Journal of Organic Chemistry, 1995 US, vol. 60, No. 20, 1995, pp. 6296-6301, XP002568731, ISSN: 0022-3263.
Seki, M. et al., "A Novel Synthesis of (+)-Biotin from L-Cysteine", Journal of Organic Chemistry, 2002, 67, 5527-5536.
Reinhold, V. et al., "Synthesis of α-N-Methylated Histidines", J Med Chem. Mar. 1968;11(2):258-60.
Askari, A. et al., "The Reaction Sequence in Ergothioneine Biosynthesis: Hercynine as an Intermediate", The Journal of Biological Chemistry, vol. 237, No. 5, May 1962.
Piez, K. et al., "Desalting of Amino Acid Solutions by Ion Exchange", (from the Department of Chemistry, Northwestern University Dental School, Chicago), downloaded from www.jbc.org on Aug. 29, 2011.
Heath, H. et al. "The Synthesis of Ergothioneine", J. Chem. Soc., 1951, 2215-2217, DOI: 10.1039/JR9510002215.
Schubert, M., "Compounds of Thiol Acids With Aldehydes", J. Biol. Chem. 1936 114: 341-350.
J. Organomet. Chem., "Regenerative Role of the Red Phosphorus in the Couple Hydriodic Acid-Red Phosphorus", 529, 295-299 (1997) [www.rhodium.ws].

* cited by examiner

*Primary Examiner* — Kamal Saeed
*Assistant Examiner* — Janet L Coppins
(74) *Attorney, Agent, or Firm* — Harness, Dickey & Pierce, P.L.C.

(57) ABSTRACT

Methods for the synthesis of 2-thiohistidine or a derivative thereof of the formula (I), or of a physiologically acceptable salt, a tautomer, a stereoisomer or a mixture of stereoisomers in any proportions thereof, from a compound of the formula (II) or a physiologically acceptable salt, a tautomer, a stereoisomer or a mixture of stereoisomers in any proportions thereof, by cleavage reaction in the presence of a thiol at a temperature higher than or equal to 60° C. The invention also relates to compounds of the formula (II) and a method for the synthesis thereof.

30 Claims, No Drawings

METHOD FOR THE SYNTHESIS OF 2-THIOHISTIDINE AND THE LIKE

CROSS-REFERENCE TO RELATED APPLICATIONS

This application is a National Phase Entry of International Application No. PCT/EP2010/064947, filed on Oct. 6, 2010, which claims priority to French Patent Application Serial No. 0956968, filed on Oct. 6, 2009, both of which are incorporated herein by reference.

BACKGROUND AND SUMMARY

The present patent application relates to a novel method for the synthesis of 2-thiohistidine and of related derivatives.

L-2-thiohistidine, also referred to as L-2-mercaptohistidine or α-amino-2,3-dihydro-2-thioxo-1H-imidazole-4-propanoic acid, has the following formula I-1:

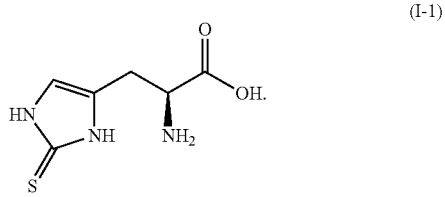 [SMILES: N[C@@H](Cc1c[nH]c(=S)[nH]1)C(=O)O]

This amino acid was obtained by acid hydrolysis of copper proteins such as molluscan hemocyanin or mushroom tyrosinase. L-2-thiohistidine is a good chelator of divalent metal ions such as $Zn^{2+}$ or $Cu^{2+}$. It is used notably in beauty care, as a depigmenting agent or as a deodorant, and also as an antioxidant for pharmaceutical, cosmetic or dietary use. In view of the interest of this compound, several syntheses of 2-thiohistidine or derivatives thereof have been described in the literature.

For example, a first synthesis describes the transformation of L-histidine methyl ester into a di-tert-butoxycarboxyl (di-Boc) derivative. The latter is then treated with phenyl chlorothionoformate which, after treatment, yields a mixture of mono- and di-Boc-2-thiohistidine methyl esters. After deprotection, L-2-thiohistidine is obtained with a total yield of 70% (J. Xu, J. C. Yadan, *J. Org. Chem.* 60, 6296-6301 (1995)).

However, such a synthesis requires protection of the histidine's amino group which cannot be present in a free form. Moreover, phenyl chlorothionoformate must be prepared from thiophosgene ($CSCl_2$), a reagent that is toxic and not readily available in large quantities for use on an industrial scale.

The international applications WO 95/18108 and WO 95/00494 describe the synthesis of Nα,Nα-dimethyl-2-thiohistidine or the ester thereof from Nα,Nα-dimethyl-histidine methyl ester by reaction with phenyl chlorothioformate, then optionally hydrolysis.

The patent application US 2009/0093642 also describes a synthesis of 2-thiohistidine (according to a method described by Heath, H. et al., J. Chem. Soc., 1951, 2215) from histidine by opening of the imidazole ring and then reaction with a thiocyanate such as KSCN. In addition to the use of large volumes of hydrochloric acid, KSCN, used in an acid medium, is a highly toxic reagent.

Shosuke Ito also described in 1985 a synthesis of 2-thiohistidine from histidine (*J. Org. Chem.* 1985, 50, 3636-3638). Thus, histidine is reacted with bromine to yield, very likely via a bromolactone, a 2-thiohistidine thioether after reaction with cysteine. A reductive hydrolysis in the presence of hydriodic acid (HI) and red phosphorus (P) then yields the expected 2-thiohistidine and (D,L)-alanine. 2-Thiohistidine can also be obtained directly from the bromolactone intermediate by reaction with $Na_2S$.

However, at the industrial level, the Ito method poses purification problems since two column chromatographies are necessary to obtain the thioether intermediate, as well as to obtain the final product, the final 2-thiohistidine being obtained with a total yield of only 12%. In addition, the use of red phosphorus is not recommended for use at the industrial level, since it is highly inflammable. Moreover, hydrogen is formed during this reaction between hydriodic acid (HI) and red phosphorus (P) (J. Organomet. Chem. 529, 295-299 (1997)) which is also very dangerous on an industrial scale.

Thus, there is a real need to develop a novel method for the synthesis of 2-thiohistidine and derivatives thereof that is applicable at the industrial level, i.e., that does not have purification difficulties, that does not use products or solvents that are dangerous or toxic for humans and the environment, and that enables access to the product, on an industrial scale, with a good yield and at a low cost.

The present invention thus has as an object a method for the synthesis of a 2-thiohistidine derivative of the following formula (I):

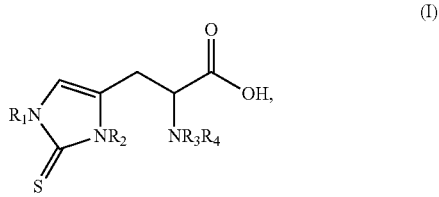

or a physiologically acceptable salt, a tautomer, a stereoisomer or a mixture of stereoisomers in any proportions thereof, in particular a mixture of enantiomers, and notably a racemic mixture thereof, wherein:

$R_1$ and $R_2$ represent, independently of each other, a hydrogen atom or a ($C_1$-$C_4$)alkyl group such as methyl, at least one of the groups $R_1$ and $R_2$ representing a hydrogen atom, and advantageously each representing a hydrogen atom, and $R_3$ and $R_4$ represent, independently of each other, a hydrogen atom or a ($C_1$-$C_4$)alkyl group such as methyl, comprising the following successive steps:

(i) cleavage reaction of a compound of following formula (II):

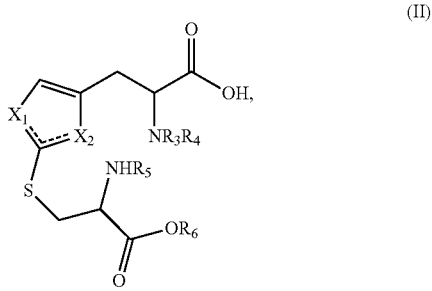

or a physiologically acceptable salt, a tautomer, a stereoisomer or a mixture of stereoisomers in any proportions thereof, in particular a mixture of enantiomers, and notably a racemic mixture thereof, wherein:

represents

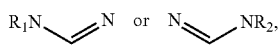

$R_1$, $R_2$, $R_3$ and $R_4$ are such as defined above, $R_5$ represents a hydrogen atom or a $(C_1\text{-}C_4)$alkyl or —CO—$((C_1\text{-}C_4)$alkyl$)$ group, and in particular a hydrogen atom or a —COCH$_3$ group, and more particularly a hydrogen atom, and $R_6$ represents a hydrogen atom or a $(C_1\text{-}C_4)$alkyl group, and in particular a hydrogen atom, in the presence of a thiol, preferably soluble in the reaction solvent, which can be notably water, at a temperature higher than or equal to 60° C., to yield the compound of the formula (I), and (ii) separation of the compound of the formula (I) obtained in the preceding step (i) from the reaction medium.

In the context of the present invention, "tautomer" refers to a structural isomer of the compound obtained by prototropy, i.e., by migration of a hydrogen atom and relocation of a double bond. The different tautomers of a compound are generally interconvertible and are present in equilibrium in solution, in proportions that can vary according to the solvent used, the temperature or the pH.

In the context of the compounds of the invention, the 2-thioimidazole ring can be present in the various tautomer forms as follows:

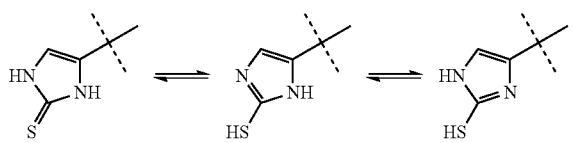

In the present invention, "physiologically acceptable" refers to that which is generally safe, nontoxic and neither biologically nor otherwise undesirable and which is acceptable for pharmaceutical, cosmetic or dietary (human or animal) use.

The "physiologically acceptable salts" of a compound refer to salts that are physiologically acceptable, such as defined above, and that have the desired activity (pharmacological, cosmetic or dietary) of the parent compound. Such salts comprise:

(1) hydrates and solvates, (2) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-1-tartaric acid, tartaric acid, p-toluenesulfonic acid, trimethylacetic acid, trifluoroacetic acid and the like, or (3) salts formed when an acid proton present in the parent compound is either replaced by a metal ion, for example an alkaline metal ion, an alkaline-earth metal ion or an aluminum ion; or coordinated with an organic or inorganic base. Acceptable organic bases comprise diethanolamine, ethanolamine, N-methylglucamine, triethanolamine, tromethamine and the like. Acceptable inorganic bases comprise aluminum hydroxide, calcium hydroxide, potassium hydroxide, sodium carbonate and sodium hydroxide.

In the context of the present invention, "stereoisomers" refer to diastereoisomers and enantiomers; they are thus optical isomers. Stereoisomers that are not mirror images of each other are referred to as "diastereoisomers," and stereoisomers that are mirror images of each another, but non-superimposable, are referred to as "enantiomers."

A mixture containing equal quantities of the two individual enantiomer forms of opposite chirality is referred to as a "racemic mixture."

In the context of the present invention, "$(C_1\text{-}C_4)$alkyl" group refers to a linear or branched saturated hydrocarbon chain comprising 1 to 4 carbon atoms. It may be a methyl, ethyl, propyl, isopropyl, butyl, isobutyl, sec-butyl or tert-butyl group. In particular, it will be a methyl group.

In the context of the present invention, "thiol" refers to any reagent containing an SH group in its molecular structure. It will be more particularly a compound of the formula R—SH, with R representing a $C_1\text{-}C_8$, notably $C_2\text{-}C_6$, linear or branched saturated hydrocarbon chain, substituted by one or more polar substituents.

In the context of the present invention, "saturated hydrocarbon chain" refers to a linear or branched saturated hydrocarbon chain, advantageously comprising 1 to 8 carbon atoms. It can be more particularly a linear saturated chain such as a methyl, ethyl, propyl, butyl, pentyl or hexyl group.

In the context of the present invention, "polar substituents" refer to hydrophilic groups such as OH, SH, NH$_2$ and COOH groups.

In the context of the present invention, "cleavage reaction" means that the compound engaged in this reaction is split into two parts during this reaction to enable formation of the thiocarbonyl functional group of the compound of the formula (I).

The compound of the formula (I) can be in particular a compound of the following formula (Ia):

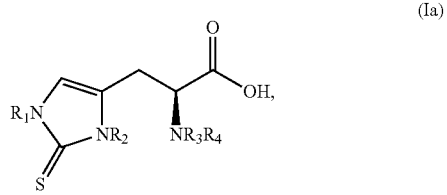

or a physiologically acceptable salt, a tautomer, a stereoisomer or a mixture of stereoisomers in any proportions thereof, in particular a mixture of enantiomers, and notably a racemic mixture thereof, wherein $R_1$, $R_2$, $R_3$ and $R_4$ are such as defined above.

The compound of the formula (I) can be notably 2-thiohistidine (notably in D or L form or a racemic D,L mixture), α-methyl-2-thiohistidine and α,α-dimethyl-2-thiohistidine, and will be in particular 2-thiohistidine and notably L-2-thiohistidine.

Step (i):

This cleavage reaction carried out in the presence of a thiol makes it possible to obtain the compound of the formula (I) as well as pyruvic acid ($CH_3C(O)$—$CO_2H$) or a derivative thereof, notably an ester ($CH_3C(O)$—$CO_2R_6$) or a derivative obtained by reaction with the thiol, such as a thioketal derivative (two thiol molecules reacting with the ketone functional group of pyruvic acid).

In contrast, the Ito reaction involves reductive hydrolysis yielding 2-thiohistidine and (D,L)-alanine and not pyruvic acid. This result can be explained by the fact that the cleavage reaction is carried out in the presence of HI and red phosphorus which generates hydrogen in situ (J. Organomet. Chem. 529, 295-299 (1997)).

The obtaining of pyruvic acid or a derivative thereof in the place of (D,L)-alanine (as obtained in the Ito method, J. Org. Chem. 1985, 50, 3636-3638) during this cleavage reaction has the advantage of facilitating subsequent purification of the compound of the formula (I) since pyruvic acid (or a derivative thereof) is soluble in organic solvents whereas (D,L)-alanine is soluble in water as are the compounds of the formula (I). Moreover, the formation of hydrogen during this reaction is strongly advised against on an industrial scale due to its explosive nature.

Furthermore, the thiol should preferably be soluble in the reaction solvent, which can be notably water, which has the additional advantage of being more ecological.

The thiol used in this step (i) can be more particularly a thiol of formula R—SH, with R representing a linear or branched, preferably linear, alkyl chain comprising from 1 to 8, notably 2 to 6, in particular 2 to 4, carbon atoms, substituted by one or more groups selected from OH, SH, $NH_2$ and COOH.

The presence of hydrophilic groups (OH, SH, $NH_2$ and COOH) will be able notably to render the thiol more soluble in water, when water is used as the solvent.

The thiol can be selected from cysteine, dithiothreitol, 2-mercaptoethanol, 2-mercaptopropionic acid, 3-mercaptopropionic acid and thioglycolic acid, and preferably will be 3-mercaptopropionic acid. It can also be mercaptoacetic acid and mercaptohexanoic acid.

Advantageously, at least 2 molar equivalents of thiol in relation to the compound (II) will be used, i.e., at least 2 moles of thiol are used for one mole of the compound (II) used. In particular, at least 5 molar equivalents of thiol, and notably 5 to 10 molar equivalents of thiol, in relation to the compound (II) can be used.

The reaction mixture is heated at a temperature higher than 60° C. because below this temperature the reaction kinetics would be too slow. The reaction can be carried out at a temperature between 60° C. and 120° C., notably between 80° C. and 100° C., more particularly after the addition of thiol. The reaction can be carried out notably in an acidic medium.

Step (ii):

The final product obtained (the compound of the formula (I)) can be separated from the reaction medium by techniques well-known to those persons skilled in the art and applicable at the industrial scale, in particular by precipitation of the compound of the formula (I) notably by adjusting the pH of the solution to arrive, for example, at a pH between 5.5 and 6.5, preferably roughly 6 (more particularly in the case of 2-thiohistidine) or by evaporation, optionally partial evaporation, of the solvents followed preferably by recrystallization to purify the product.

The compounds of the formula (I) being water soluble, one or more preliminary extractions with an organic solvent, such as ethyl acetate or tert-butyl-methyl ether, will make it possible to eliminate the organic by-products formed during the reaction, such as pyruvic acid or derivatives thereof, as well as excess thiol.

The product obtained can be purified if necessary by techniques well-known to those persons skilled in the art, for example by recrystallization. Before or after this step (ii), a salt of the compound formed can be prepared, if so desired, notably by the addition of a physiologically acceptable acid or base such as defined above.

The compound of the formula (II) can be prepared from an acid addition salt, with the exception of a hydriodic acid (HI) salt, of the compound of the following formula (III):

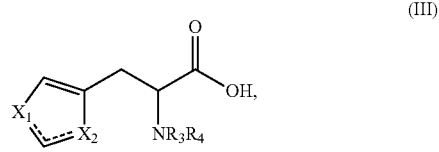

(III)

or a tautomer or a stereoisomer or a mixture of stereoisomers in any proportions thereof, in particular a mixture of enantiomers, and notably a racemic mixture thereof,
wherein

$R_3$ and $R_4$ are such as defined above,
by successive reaction with bromine,
and then with a cysteine derivative of the following formula (IV):

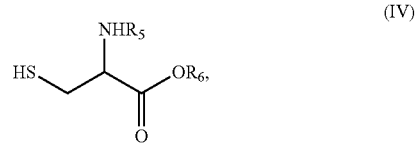

(IV)

or a stereoisomer or a mixture of stereoisomers in any proportions thereof, in particular a mixture of enantiomers, and notably a racemic mixture thereof, wherein $R_5$ and $R_6$ are such as defined above.

In the context of the present invention, "acid addition salt of the compound of the formula (III)" refers to a salt of the compound of the formula (III) obtained by addition of an acid, to the exclusion of hydriodic acid (HI). The acid can be in particular hydrochloric acid or sulfuric acid.

In this reaction, bromine can be used in a ratio of 1 to 1.5 molar equivalents in relation to the compound of the formula (III). Preferably, the bromine is added cold (very rapid addition, preferably), at a temperature lower than 10° C., preferably lower than 5° C. The addition of bromine can thus be carried out at a temperature between −10° C. and 10° C., advantageously between −5° C. and 5° C.

The cysteine derivative can be in particular N-acetylcysteine or cysteine (notably in D, L or racemic form), and in particular cysteine and notably L-cysteine. The cysteine derivative will advantageously be used in excess, in particular in a ratio of 2 to 7, advantageously 3 to 5, molar equivalents of the cysteine derivative in relation to the compound of the formula (III), i.e., from 2 to 7, advantageously 3 to 5, moles of cysteine derivative are used per mole of the compound (III) used. This reaction can be carried out in a solvent such as water. The yield of this step can be equal to or higher than 50%, even equal to or higher than 70%.

Preferably, the compound of the formula (II) will not be isolated from the reaction medium but will be engaged directly in the following step (i). Thus, the preparation of the compound (I) from the compound (III) can be carried out in a single reactor, without isolation of the intermediate compound (II) (one-pot reaction).

The method for the preparation of a compound of the formula (I) according to the invention will thus comprise the following successive steps:

(a1) reaction of an acid addition salt, to the exclusion of a hydriodic acid salt, of a compound of the formula (III) such as defined above, or a tautomer, a stereoisomer or a mixture of stereoisomers in any proportions thereof, in particular a mixture of enantiomers, and notably a racemic mixture thereof, with bromine,
and then with a cysteine derivative of the formula (IV) such as defined above or a stereoisomer or a mixture of stereoisomers in any proportions thereof, in particular a mixture of enantiomers, and notably a racemic mixture thereof, and in particular with cysteine and notably L-cysteine,
to yield a compound of the formula (II) such as defined above, (b1) cleavage reaction of the compound of the formula (II) obtained in the preceding step (a1) in the presence of a thiol such as defined above, preferably soluble in the reaction solvent, which can be notably water, at a temperature higher than or equal to 60° C., to yield a compound of the formula (I), and (c1) separation of the compound of the formula (I) obtained in the preceding step (b1) from the reaction medium.

The steps (b1) and (c1) correspond to the preceding steps (i) and (ii), respectively. Step (a1) corresponds to the preparation step of the compound of the formula (II) described above. Advantageously, steps (a1) and (b1) will be carried out in the same solvent, such as water, preferably, in the same reactor, i.e., without isolation of the intermediate products (the compound of the formula (II) in particular).

Under these conditions, the reaction medium will contain a cysteine derivative used preferably in excess in the step (a1). Before separating the compound of the formula (I) from the reaction medium (step (c1)), it can thus be necessary to eliminate excess cysteine derivative in order to facilitate the isolation and purification of the compound of the formula (I). Notably, in the case of a cysteine derivative wherein $R_5$=H or $(C_1-C_4)$alkyl such as cysteine, benzaldehyde for example can be added to then form with the excess cysteine derivative a 2-phenylthiazolidine-4-carboxylic acid derivative, a compound which precipitates in a solvent such as water. By this means, the excess cysteine derivative can be recycled.

The total yield of the compound of the formula (I) prepared from the compound of the formula (III) can be equal to or higher than 40%.

According to a particular embodiment of the invention, the compound of the formula (I) is a compound of the formula (Ia) and the method for preparing same comprises the following successive steps:

(a2) reaction of an acid addition salt, to the exclusion of a hydriodic acid salt, of a compound of the following formula (IIIa):

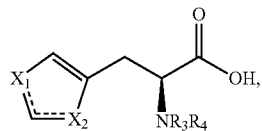
(IIIa)

or a tautomer or a stereoisomer or a mixture of stereoisomers in any proportions thereof, in particular a mixture of enantiomers, and notably a racemic mixture thereof,
wherein

$R_3$ and $R_4$ are such as defined above,
with bromine,
and then with a cysteine derivative of the formula (IV) such as defined above or a stereoisomer or a mixture of stereoisomers in any proportions thereof, in particular a mixture of enantiomers, and notably a racemic mixture thereof, and in particular with cysteine and notably L-cysteine,
to yield a compound of the following formula (IIa):

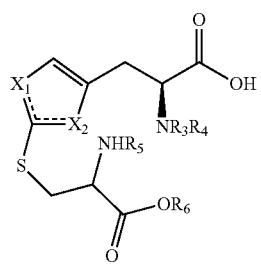
(IIa)

or a physiologically acceptable salt, a tautomer, a stereoisomer or a mixture of stereoisomers in any proportions thereof, in particular a mixture of enantiomers, and notably a racemic mixture thereof,
wherein

$R_3$, $R_4$, $R_5$ and $R_6$ are such as defined above, (b2) cleavage reaction of the compound of the formula (IIa) obtained in the preceding step (a2) in the presence of a thiol such as defined above, preferably soluble in the reaction solvent, which can be water, and in particular with cysteine, dithiothreitol, 2-mercaptoethanol, 2-mercaptopropionic acid, 3-mercaptopropionic acid or thioglycolic acid, and preferably with 3-mercaptopropionic acid, at a temperature higher than or equal to 60° C., to yield a compound of the formula (Ia), and (c2) separation of the compound of the formula (Ia) obtained in the preceding step (b2) from the reaction medium.

The steps (a2), (b2) and (c2) correspond to the preceding steps (a1), (b1) and (c1), respectively. The compounds of the formula (IIa) represent particular forms of the compound of the formula (II). Similarly, the compounds of the formula (IIIa) represent particular forms of the compound of the formula (III).

The present invention also has as an object a compound of the following formula (II):

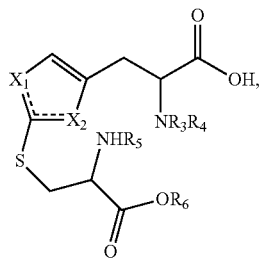
(II)

or a physiologically acceptable salt, a tautomer, a stereoisomer or a mixture of stereoisomers in any proportions thereof, in particular a mixture of enantiomers, and notably a racemic mixture thereof, wherein:

represents

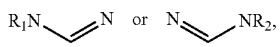

and
$R_1$, $R_2$, $R_3$, $R_4$, $R_5$ and $R_6$ are such as defined above, to the exclusion of compound wherein

represents

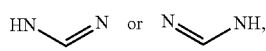

and $R_3$ and $R_4$ each represent a hydrogen atom.

The excluded compound is described in: Ito et al., *J. Org. Chem.* 1985, 50, 3636-3638. This compound can be in particular 2-{2-[(2-ammonio-2-carboxyethyl)thio]-1H-imidazol-4-yl}-1-carboxy-N,N-dimethylethanaminium (His-NMe$_2$-Cys) or the dihydrochloride thereof, and 2-{2-[(2-ammonio-2-carboxyethyl)thio]-1H-imidazol-4-yl}-1-carboxy-N-methylethanaminium (HisNHMe-Cys) or the dihydrochloride thereof.

The present invention also has as an object a method for the preparation of a compound of the following formula (II):

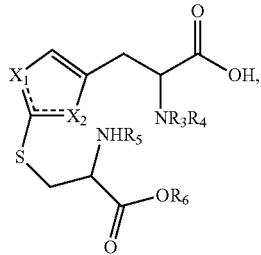
(II)

or a physiologically acceptable salt, a tautomer, a stereoisomer or a mixture of stereoisomers in any proportions thereof, in particular a mixture of enantiomers, and notably a racemic mixture thereof, wherein:

represents

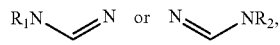

and
$R_1$, $R_2$, $R_3$, $R_4$, $R_5$ and $R_6$ are such as defined above, by reaction of an acid addition salt, to the exclusion of a hydriodic acid salt, of a compound of the formula (III) such as defined above, or a tautomer, a stereoisomer or a mixture of stereoisomers in any proportions thereof, in particular a mixture of enantiomers, and notably a racemic mixture thereof, with bromine, and then with 2 to 7, preferably 3 to 5, molar equivalents, in relation to the compound of the formula (III), of a cysteine derivative of the formula (IV) such as defined above, and in particular cysteine and notably L-cysteine.

In this reaction, the bromine can be used in a ratio of 1 to 1.5 molar equivalents in relation to the compound of the formula (III). Preferably, the bromine is added cold (very rapid addition, preferably), at a temperature lower than 10° C., preferably lower than 5° C. The addition of bromine can thus be carried out at a temperature between −10° C. and 10° C., advantageously between −5° C. and 5° C. This reaction can be carried out in a solvent such as water.

DETAILED DESCRIPTION

The present invention will be better understood in the light of the examples which follow, which are provided for illustrative purposes only and in no way limit the scope of the invention.

EXAMPLES

All the reactions were carried out in the open air unless otherwise specified.

1-Preparation of Compounds of the Formula (II) of the Invention

Example 1

Preparation of 2-{2-[(2-ammonio-2-carboxyethyl)thio]-1H-imidazol-4-yl}-1-carboxy-ethanaminium dihydrochloride (His-Cys, 2HCl)

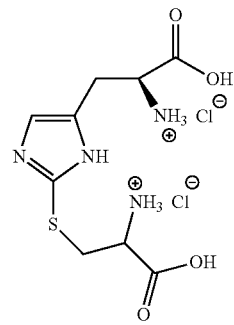 [SMILES: [NH3+]C(CSc1ncc(C[C@H]([NH3+])C(=O)O)[nH]1)C(=O)O ; [Cl-] ; [Cl-]]

1.57 g (7.5 mmol) of L-histidine hydrochloride monohydrate is dissolved in 15 ml of water and the solution is cooled at 0° C. Under very strong stirring, 500 µl (1.56 g, 9.75 mmol, 1.3 eq) of bromine is added dropwise (addition time: 2 min 10 sec). The reaction mixture turns yellow. Three minutes after the end of the addition of bromine, 2.81 g (22.5 mmol, 3 eq) of L-cysteine is added. Immediately, the mixture loses its color. After stirring at 0° C. for 1 hour, the mixture is filtered and the precipitate is washed with 2×0.5 ml of water.

The filtrate is deposited on a column filled with 75 g of Dowex® 50WX2-400, conditioned beforehand with 1 N hydrochloric acid (HCl). After elution with 750 ml of 1 N hydrochloric acid and then 500 ml of 2 N hydrochloric acid, the fractions containing the desired product are combined. After evaporation and two co-evaporations with 2×20 ml of toluene, 1.5 g (56%) of the desired product in the form of yellow crystals is obtained after drying.

$^1$H-NMR (D$_2$O/DCl, 400 MHz): δ (ppm)=3.32 (m, 2H); 3.63 (m, 2H); 4.22 (m, 2H); 7.39 (s, 1H).

UPLC-MS (ES+): 275.8 (MH+)

Example 2

Preparation of 2-{2-[2-ammonio-2-carboxyethyl)thio]-1H-imidazol-4-yl}-1-carboxy-N,N-dimethyl-ethanaminium dihydrochloride (HisNMe$_2$-Cys, 2HCl)

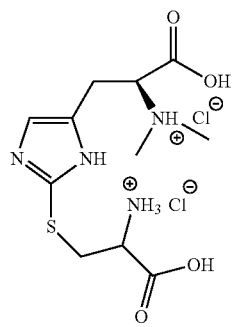 [SMILES: C[NH+](C)[C@@H](Cc1cnc(SCC([NH3+])C(=O)O)[nH]1)C(=O)O ; [Cl-] ; [Cl-]]

4.753 g (20 mmol) of N,N-dimethylhistidine hydrochloride monohydrate (V. N. Reinhold et al., *J. Med. Chem.* 11, 258 (1968)) is dissolved in 40 ml of water and the solution is cooled at 0° C. Under very strong stirring, 1.23 ml (3.835 g, 24 mmol, 1.2 eq) of bromine is rapidly added dropwise (addition time: 1 min 20 sec), without exceeding 2° C. The reaction mixture turns yellow and a reddish solid is formed. Seven minutes after the end of the addition of bromine, all the red solid dissolves and then 7.417 g (60 mmol, 3 eq) of L-cysteine is added. Immediately, the mixture loses its color. After stirring at 0° C. for 1 hour, a white suspension is obtained. The mixture is filtered and the precipitate is washed with 2×2 ml of water.

The filtrate is deposited on a column filled with 100 g of Dowex® 50WX2-400, conditioned beforehand with 1 N hydrochloric acid (HCl). After elution with 800 ml of 1 N hydrochloric acid and then 1000 ml of 2 N hydrochloric acid, the fractions containing the desired product are combined. After evaporation and two co-evaporations with 2×50 ml of toluene, 4.84 g (63%) of the desired product in the form of slightly yellow crystals is obtained after drying.

$^1$H-NMR (D$_2$O, 400 MHz): δ (ppm)=2.86 (s, 6H); 3.32 (m, 2H); 3.61 (m, 2H); 4.21 (m, 1H); 4.32 (m, 1H); 7.37 (s, 1H).

UPLC-MS (ES+): 303.8 (MH+)

Example 3

Preparation of 2-{2-[(2-ammonio-2-carboxyethyl)thio]-1H-imidazol-4-yl}-1-carboxy-N-methylethanaminium dihydrochloride (HisNHMe-Cys, 2HCl)

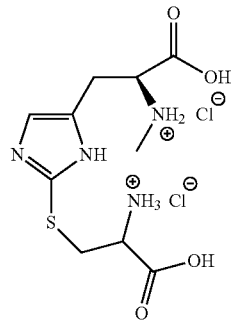 [SMILES: C[NH2+][C@@H](Cc1cnc(SCC([NH3+])C(=O)O)[nH]1)C(=O)[O-] ; [Cl-] ; [Cl-]]

1.187 g (5.656 mmol) of α-N-methylhistidine hydrochloride (V. N. Reinhold et al., *J. Med. Chem.* 11, 258 (1968)) is dissolved in 11.3 ml of demineralized water. The solution is cooled at 0° C. and 377 µl (1.175 g, 7.353 mmol, 1.3 eq) of bromine is added dropwise under very strong stirring (addition time: 1 min 45 sec). The reaction mixture turns yellow and the temperature increases to 4° C.

Three minutes after the end of the addition of bromine, 2.119 g (16.96 mmol, 3 eq) of L-cysteine is added. Immediately, the mixture loses its color. After stirring at 0° C. for 1 hour, the mixture is deposited on a column filled with 50 g of Dowex® 50WX2-400, conditioned beforehand with 0.5 N hydrochloric acid. After elution with 250 ml of 0.5 N hydrochloric acid and then 250 ml of 1 N hydrochloric acid and 500 ml of 1.5 N hydrochloric acid, the fractions containing the desired product are combined. After evaporation and drying under vacuum (20 mbar), 1.427 g (68%) of the desired product in the form of yellow crystals is obtained.

$^1$H-NMR (D$_2$O, 400 MHz): δ (ppm)=2.71 (s, 3H); 3.33 (m, 2H); 3.62 (m, 2H); 4.08 (m, 1H); 4.28 (m, 1H); 7.40 (s, 1H).

UPLC-MS (ES+): 289.8 (MH+)

2—Preparation of Compounds of the Formula (I) of the Invention (Without Isolation of the Intermediates of the Formula (II))

2-1—Preparation of 2-thiohistidine

Example 4

One-pot preparation of L-2-thiohistidine from histidine

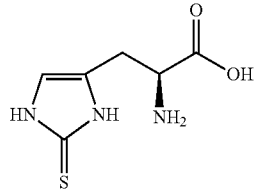 [SMILES: N[C@@H](Cc1c[nH]c(=S)[nH]1)C(=O)O]

a) Synthesis of the His-Cys Intermediate (Compound of the Formula (II))

317.6 g (1.5 mol) of L-histidine hydrochloride monohydrate is dissolved in 3 liters of demineralized water. The solution is transferred to a double-walled glass reactor with mechanical stirring and is cooled at −4° C. Under very strong stirring, 100.2 ml (311.6 g, 1.95 mol, 1.3 eq) of bromine is added very quickly via a bromine vial, without exceeding 4° C. (addition time: 2 min 50 sec). The reaction mixture turns yellow-orange but remains clear and homogeneous. Three minutes after the end of the addition of bromine, 562 g (4.5 mol, 3 eq) of L-cysteine is added and the internal temperature increases to 12° C. Immediately, the mixture loses its color. After several minutes the solution becomes slightly yellow. C After stirring at 0° C. for 1 hour, analysis of a sample by $^1$H-NMR (D$_2$O) shows that the His-Cys adduct is formed with a reaction yield of 70%. The cooling system is turned off and the reaction mixture is allowed to stir for 1 hour. The internal temperature increases to 12° C. The His-Cys adduct is not isolated and is engaged directly in the following step.

b) Synthesis of L-2-thiohistidine 793.4 ml (960 g, 9 mol, 6 eq) of 3-mercaptopropionic acid is then added to the mixture, which is then heated under strong stirring at 100° C. for 18 h. Analysis of a sample by $^1$H-NMR (D$_2$O) shows that the His-Cys adduct is completely cleaved into L-2-thiohistidine.

c) Isolation of L-2-thiohistidine

After cooling at room temperature, the dark-brown mixture is extracted with 4×3 l of ethyl acetate. The aqueous phase is retained and placed under a strong stream of nitrogen in a 40° C. bath. The pH of the mixture is adjusted to 8.5 by rapidly adding 20% aqueous ammonia solution (roughly 580 ml). Still under nitrogen, 37% concentrated hydrochloric acid is then added dropwise (roughly 120 ml) until a pH of 6.5 is reached. A colorless precipitate forms during the addition of the acid, and the suspension is maintained for 1 hour at 40° C. under stirring (under nitrogen).

After filtration and washing with 3×300 ml of demineralized water, followed by 2 washings with 600 ml of absolute ethanol and 3×600 ml of n-pentane, the solid obtained is dried over P$_2$O$_5$ under vacuum (20 mbar). 130.1 g (45%) of L-2-thiohistidine in the form of a white powder is obtained.

The analytical data of the product obtained are identical to those in the literature (J. Xu, J. C. Yadan, *J. Org. Chem.* 60, 6296-6301 (1995)).

$[\alpha]_D$: −11.0 (c=1.0; 1 N HCl)
$^1$H-NMR (D$_2$O/DCl, 400 MHz): δ (ppm)=3.10 (m, 2H); 4.20 (m, 1H); 6.77 (s, 1H).
UPLC-MS (ES+): 188.6 (MH+)

The following examples 5 to 8 show the variability of the acid addition salt of the compound of the formula (III) which can be used, as well as the variability of the thiol which can be used. These examples are for illustrative purposes only and in no way limit the scope of the present invention.

Example 5

One-Pot Preparation of L-2-thiohistidine from L-Histidine-Acid Addition Salt Variation The procedure is as described in example 2, except that 5 g (32.2 mmol) of L-histidine is used, dissolved in 65 ml of water and 900 μl (1.66 g, 16.1 mmol, 1 eq) of 98% sulfuric acid. 2.72 g (45%) of L-2-thiohistidine in the form of a white powder is obtained. $^1$H-NMR (D$_2$O/DCl) analysis is identical to that described in example 1.

Example 6

One-Pot Preparation of L-2-Thiohistidine from L-Histidine-Thiol (Mercaptoacetic Acid) Variation 3.5 g (16.52 mmol) of L-histidine hydrochloride monohydrate is dissolved in 33 ml of water and the solution is cooled at −3° C. Under very strong stirring, 1.1 ml (3.433 g, 21.48 mmol, 1.3 eq) of bromine is rapidly added dropwise (addition time: 3 min). The reaction mixture turns yellow. Three minutes after the end of the addition of bromine, 6.19 g (49.58 mmol, 3 eq) of L-cysteine is added. Immediately, the mixture loses its color. After stirring at 0° C. for 30 min, 7.13 ml (9.4 g, 99.17 mmol) of mercaptoacetic acid is added and then the solution while stirring is heated at 80° C. for 40 h.

For the isolation of L-2-thiohistidine, the procedure is as described in example 1. 43% of L-2-thiohistidine in the form of a cream-white powder is obtained. $^1$H-NMR (D$_2$O/DCl) analysis is identical to that described in example 1.

Example 7

One-Pot Preparation of L-2-Thiohistidine from L-Histidine-Thiol (Mercaptohexanoic Acid) Variation 257 mg (1.21 mmol) of L-histidine hydrochloride monohydrate is dissolved in 2.4 ml of water and the solution is cooled at −3° C. Under very strong stirring, 80 μl (252 mg, 1.58 mmol, 1.3 eq) of bromine is rapidly added dropwise. The reaction mixture turns yellow. Three minutes after the end of the addition of bromine, 455 mg (3.64 mmol, 3 eq) of L-cysteine is added. Immediately, the mixture loses its color. After stirring at 0° C. for 1 hour, 933 μl (1.0 g, 6.07 mmol) of mercaptohexanoic acid is added and then the solution while stirring is heated at 80° C. for 40 h. $^1$H-NMR (D$_2$O) analysis of a sample shows that the His-Cys adduct is completely cleaved into L-2-thiohistidine.

Example 8

One-Pot Preparation of L-2-Thiohistidine from L-Histidine-Thiol (Dithiothreitol) Variation 10.72 g (50.62 mmol) of L-histidine hydrochloride monohydrate is dissolved in 100 ml of water and the solution is cooled at 0° C. Under very strong stirring, 3.38 ml (10.51 g, 65.81 mmol, 1.3 eq) of bromine is rapidly added dropwise (addition time: 3 min 20 sec) without exceeding 1° C. The reaction mixture turns yellow. Three minutes after the end of the addition of bromine, 18.96 g (151.8 mmol, 3 eq) of L-cysteine is added. Immediately, the mixture loses its color. After stirring at 0° C. for 1 hour, 47.08 g (303.7 mmol, 6 eq) of dithiothreitol is added, and then the solution while stirring is heated at 80° C. for 40 h. For the isolation of L-2-thiohistidine, the procedure is as described in example 1. 41% of L-2-thiohistidine in the form of a white powder is obtained.

$^1$H-NMR (D$_2$O/DCl) analysis is identical to that described in example 1.

Example 9

One-Pot Preparation of D-2-Thiohistidine from D-Histidine

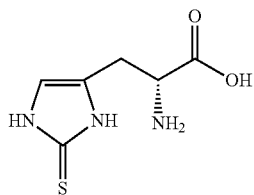 [SMILES: N[C@H](Cc1c[nH]c(=S)[nH]1)C(=O)O]

The procedure is as described in example 2-1, except that 10.32 g (65.84 mmol) of D-histidine is used, dissolved in 132 ml of water and 5.5 ml (6.48 g, 65.84 mmol) of concentrated hydrochloric acid. 4.4 g (35%) of D-2-thiohistidine in the form of a white powder is obtained. $^1$H-NMR (D$_2$O/DCl) analysis is identical to that described in example 1.

$[\alpha]_D$: +10.5 (c=1.0; 1 N HCl)

Example 10

One-Pot Preparation of D,L-2-Thiohistidine from D,L-Histidine

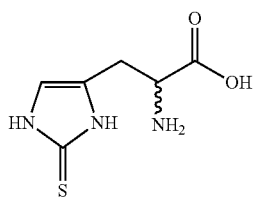 [SMILES: NC(Cc1c[nH]c(=S)[nH]1)C(=O)O]

a) Synthesis of the His-Cys Adduct 10.65 g (50.8 mmol) of D,L-histidine hydrochloride monohydrate is dissolved in 100 ml of demineralized water. The solution is cooled at −3° C. Under very strong stirring, 3.43 ml (10.66 g, 66 mmol, 1.3 eq) of bromine is added very quickly via a bromine vial, without exceeding 1° C. (addition time: 2 min 40 sec). The reaction mixture turns yellow-orange but remains clear and homogeneous. Three minutes after the end of the addition of bromine, 19.03 g (152.4 mol, 3 eq) of L-cysteine is added and the internal temperature increases to 4° C. Immediately, the mixture loses its color. After several minutes the solution becomes slightly yellow. After stirring at 0° C. for 1 hour, analysis by $^1$H-NMR (D$_2$O) of a sample shows that the His-Cys adduct is formed with a reaction yield of 72%.

The cooling bath is removed and the reaction mixture is allowed to stir for 30 min. The internal temperature increases to 10° C.

b) Synthesis of D,L-2-Thiohistidine 27 ml (32.68 g, 304.8 mol, 6 eq) of 3-mercaptopropionic acid is then added to the mixture, which is then heated under strong stirring at 80° C. for 30 h. Analysis of a sample by $^1$H-NMR (D$_2$O) shows that the His-Cys adduct is completely cleaved into 2-thiohistidine.

c) Isolation of D,L-2-Thiohistidine

After cooling at room temperature, the dark-brown mixture is extracted with 4×100 ml of ethyl acetate.

The aqueous phase is retained and placed under a strong stream of nitrogen in a 40° C. bath. The pH of the mixture is adjusted to 6 by quickly adding 20% aqueous ammonia solution. A colorless precipitate is formed, and the suspension is maintained for 25 min at 40° C. under stirring (under nitrogen).

After filtration and washing with 3×15 ml of demineralized water, followed by 2 washings with 15 ml of absolute ethanol and 3×15 ml of n-pentane, the solid obtained is dried over P$_2$O$_5$ under vacuum (20 mbar). 5.2 g of D,L-2-thiohistidine in the form of a white powder, containing roughly 10% cysteine, is obtained.

The product is purified by an acid-base treatment: 585 mg (3.79 mmol) of dithiothreitol is dissolved in 100 ml of demineralized water and then the product previously obtained (5.2 g) is added. The suspension is placed under nitrogen in a 40° C. water bath and 10 ml (11.84 g) of concentrated hydrochloric acid is added very slowly dropwise until the solid dissolves completely. The pH is then adjusted to 6 by the slow addition of 3 ml (2.735 g) of 20% aqueous ammonia solution. A fine colorless precipitate slowly forms and the suspension is maintained under stirring for 1 hour.

After filtration and washing with 3×10 ml of demineralized water followed by 3 washings with 10 ml of absolute ethanol and 3×10 ml of n-pentane, the solid obtained is dried over P$_2$O$_5$ under vacuum (20 mbar). 3.82 g (39%) of D,L-2-thiohistidine in the form of a white powder is obtained.

$^1$H-NMR (D$_2$O/DCl) analysis is identical to that described in example 1.

$[\alpha]_D$: 0 (c=1.0; 1 N HCl)

2-2—Preparation of 2-Thiohistidine Derivatives

Example 11

One-Pot Preparation of α,α-dimethyl-2-thiohistidine from α,α-dimethyl-histidine

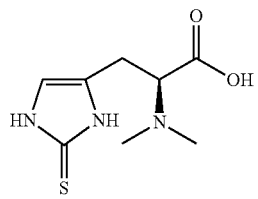

a) Preparation of the HisNMe$_2$-Cys Adduct (Compound of the Formula (II))

23.76 g (0.1 mol) of α,α-dimethylhistidine hydrochloride monohydrate (V. N. Reinhold et al., *J. Med. Chem.* 11, 258 (1968)) is dissolved in 200 ml of water. The solution is cooled at −3° C., and under very strong stirring 6.68 ml (20.77 g, 130 mmol, 1.3 eq) of bromine is added quickly dropwise without exceeding 3° C. (addition time: 4 min). The reaction mixture turns yellow and a reddish solid is formed. Seven minutes after the end of the addition of bromine the red solid completely dissolves and 37.08 g (0.3 mol, 3 eq) of L-cysteine is added. The internal temperature rises from 0° C. to 1° C. and the mixture immediately loses its color.

After stirring at 0° C. for 1 hour, analysis of a sample by $^1$H-NMR (D$_2$O) shows that the His NMe$_2$-Cys adduct forms with a reaction yield of 63%. The ice bath is removed and the reaction mixture is allowed to stir for 1 hour. The internal temperature increases to 10° C.

b) Preparation of α,α-dimethyl-2-thiohistidine 87.7 ml (106 g, 10 eq) of 3-mercaptopropionic acid is then added to the mixture, which is heated under strong stirring at 80° C. for 24 h.

Analysis of a sample by $^1$H-NMR (D$_2$O) shows that the His NMe$_2$-Cys product is cleaved completely.

c) Isolation of α,α-dimethyl-2-thiohistidine

After cooling at room temperature, the orange mixture is extracted with 4×400 ml of ethyl acetate.

The aqueous phase is retained and the pH is adjusted to 4.5-5 with 20% aqueous ammonia solution (roughly 21 ml). In order to trap the excess cysteine present in the medium, 30.5 ml (31.8 g, 3 eq) of benzaldehyde is added (according to M. P. Schubert, *J. Biol. Chem.* 114, 341-350 (1936) or M. Seki et al., *J. Org. Chem.* 67 (16), 5532 (2002)). The mixture is stirred at room temperature for 15 h and 2-phenylthiazolidine-4-carboxylic acid precipitates in the form of a light yellow solid. After filtration of the solid and rinsing with 4×40 ml of water, the filtrate is extracted with 2×200 ml of ethyl acetate.

The aqueous phase is retained and the pH is adjusted to 6 with 20% aqueous ammonia solution (roughly 2 ml). The mixture is then evaporated dry and the solid obtained is recrystallized in water. 7.28 g (33%) of the desired product in the form of a white powder is obtained.

The analytical data are identical to those described in the literature (WO 95/18108).

$^1$H-NMR (D$_2$O/DCl, 400 MHz): δ (ppm)=2.87 (s, 6H); 3.20 (m, 2H); 4.19 (m, 1H); 6.78 (s, 1H).

HPLC-MS (ES+): 216.5 (MH+)

Example 12

One-Pot Preparation of α-methyl-2-thiohistidine from α-methylhistidine

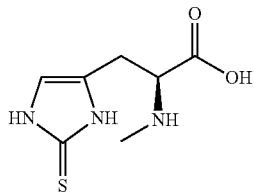

11.93 g (54.5 mmol) of α-methylhistidine hydrochloride (V. N. Reinhold et al., *J. Med. Chem.* 11, 258 (1968)) is dissolved in 109 ml of water and then the solution is cooled at 0° C. Under very strong stirring, 3.64 ml (11.33 g, 70.9 mmol, 1.3 eq) of bromine is added dropwise without exceeding 5° C. (addition time: 2 min 30 sec). The reaction mixture turns yellow. Three minutes after the end of the addition of bromine, 20.22 g (163.6 mmol, 3 eq) of L-cysteine is added and the internal temperature increases to 8° C. Immediately, the mixture loses its color. After stirring at 0° C. for 1 hour, 28.84 ml (34.9 g, 6 eq) of 3-mercaptopropionic acid is added to the mixture, which is heated under strong stirring at 100° C. for 20 h.

By continuing the protocol analogously to example 11, 5.398 g (48%) of α-methyl-2-thiohistidine in the form of a white powder is obtained.

$^1$H-NMR (D$_2$O, 400 MHz): δ (ppm)=2.65 (s, 3H); 3.15 (m, 2H); 4.12 (m, 1H); 6.77 (s, 1H).

$^{13}$C-NMR (D$_2$O, 400 MHz): δ (ppm)=24.8; 32.3; 60.0; 116.4; 123.2; 156.9; 170.0.

UPLC-MS (ES+): 202.7 (MH+)

The invention claimed is:
1. A method for the synthesis of a 2-thiohistidine derivative of the following formula (I):

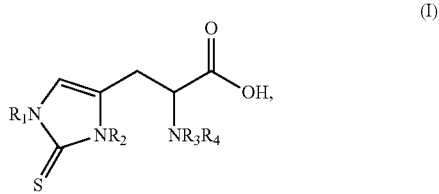

or a physiologically acceptable salt, a tautomer, a stereoisomer or a mixture of stereoisomers in any proportions thereof, wherein:
R$_1$ and R$_2$ represent, independently of each other, a hydrogen atom or a (C$_1$-C$_4$)alkyl group, at least one of the groups R$_1$ and R$_2$ representing a hydrogen atom, and
R$_3$ and R$_4$ represent, independently of each other, a hydrogen atom or a (C$_1$-C$_4$)alkyl group,
comprising the following successive steps:
(i) performing a cleavage reaction of a compound of following formula (II):

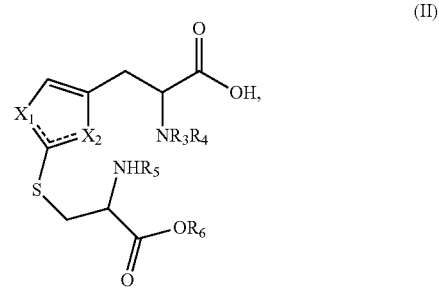

or a physiologically acceptable salt, a tautomer, a stereoisomer or a mixture of stereoisomers in any proportions thereof, wherein:

represents

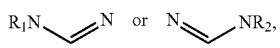

$R_1$, $R_2$, $R_3$ and $R_4$ are such as defined above, $R_5$ represents a hydrogen atom or a $(C_1\text{-}C_4)$alkyl or —CO—$((C_1\text{-}C_4)$alkyl) group, and $R_6$ represents a hydrogen atom or a $(C_1\text{-}C_4)$alkyl group, in the presence of a thiol, at a temperature higher than or equal to 60° C., to yield a compound of the formula (I), and (ii) separating the compound of the formula (I) obtained in the preceding step (i) from the reaction medium.

2. The method of claim 1, wherein the thiol has the formula R—SH, with R representing a linear or branched alkyl chain comprising from 1 to 8 carbon atoms, substituted by one or more groups selected from OH, SH, $NH_2$ and COOH.

3. The method of claim 2, wherein the thiol is selected from cysteine, dithiothreitol, 2-mercaptoethanol, 2-mercaptopropionic acid, 3-mercaptopropionic acid, mercaptoacetic acid, mercaptohexanoic acid and thioglycolic acid.

4. The method of claim 1, wherein the step (i) is carried out at a temperature between 60° C. and 120° C.

5. The method of claim 1, wherein the compound of the formula (I) has the following formula (Ia):

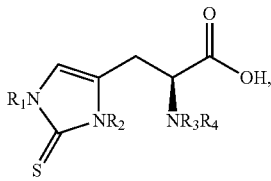

(Ia)

or a physiologically acceptable salt, a tautomer, a stereoisomer or a mixture of stereoisomers in any proportions thereof, wherein $R_1$, $R_2$, $R_3$ and $R_4$ are such as defined in claim 1.

6. The method of claim 1, wherein the compound of the formula (I) represents 2-thiohistidine, α-methyl-2-thiohistidine or α,α-dimethyl-2-thiohistidine.

7. The method of claim 1, wherein the compound of the formula (II) is prepared from an acid addition salt, to the exclusion of a hydriodic acid salt, of the compound of the following formula (III):

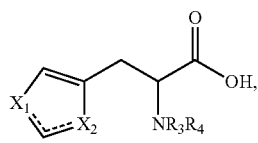

(III)

or a tautomer or a stereoisomer or a mixture of stereoisomers in any proportions thereof,
wherein

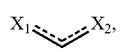

$R_3$ and $R_4$ are such as defined in claim 1, by successive reaction with bromine,
and then with a cysteine derivative of the following formula (IV):

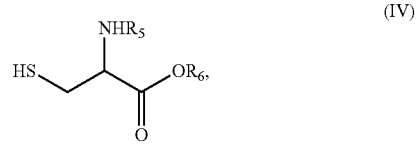

(IV)

or a stereoisomer or a mixture of stereoisomers in any proportions thereof, wherein $R_5$ and $R_6$ are such as defined in claim 1.

8. The method of claim 7, wherein the compound of the formula (I) has the formula (Ia) as defined in claim 5 and wherein the method comprises the following successive steps:

(a2) reacting an acid addition salt, to the exclusion of a hydriodic acid salt, of a compound of the following formula (IIIa):

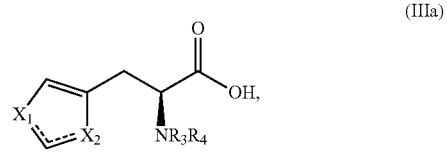

(IIIa)

or a stereoisomer or a mixture of stereoisomers in any proportions thereof, wherein

$R_3$ and $R_4$ are such as defined in claim 1, with bromine,
and then with a cysteine derivative of the formula (IV) such as defined in claim 7 or a stereoisomer or a mixture of stereoisomers in any proportions thereof,
to yield a compound of the following formula (IIa):

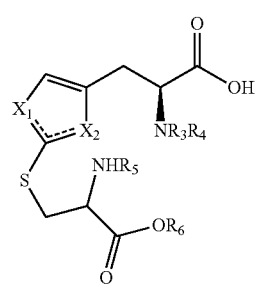

(IIa)

or a physiologically acceptable salt, a tautomer, a stereoisomer or a mixture of stereoisomers in any proportions thereof, wherein

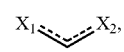

21

$R_3$, $R_4$, $R_5$ and $R_6$ are such as defined in claim 1, (b2) performing a cleavage reaction of the compound of the formula (IIa) obtained in the preceding step (a2) in the presence of a thiol, at a temperature higher than or equal to 60° C., to yield a compound of the formula (Ia), and (c2) separating the compound of the formula (Ia) obtained in the preceding step (b2) from the reaction medium.

9. The method of claim 7, wherein the cysteine derivative of the formula (IV) is used in excess, in a ratio of 2 to 7 molar equivalents of the cysteine derivative in relation to the compound of the formula (III).

10. The method of claim 7, wherein bromine is used in a ratio of 1 to 1.5 molar equivalents in relation to the compound of the formula (III).

11. The method of claim 7, wherein the preparation of the compound (I) from the compound (III) is carried out in a single reactor, without isolation of the intermediate compound (II).

12. A compound of the following formula (II):

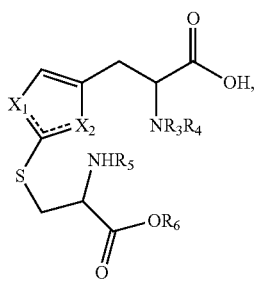

(II)

or a physiologically acceptable salt, a tautomer, a stereoisomer or a mixture of stereoisomers in any proportions thereof, wherein:

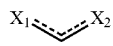

represents

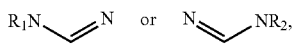

and $R_1$, $R_2$, $R_3$, $R_4$, $R_5$ and $R_6$ are such as defined in claim 1, to the exclusion of compound wherein

represents

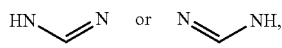

and $R_3$, $R_4$, $R_5$ and $R_6$ each represent a hydrogen atom.

22

13. A method for the preparation of a compound of the following formula (II):

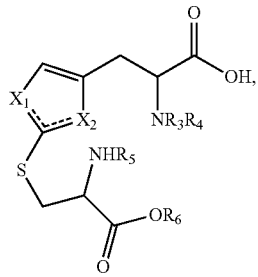

(II)

or a physiologically acceptable salt, a tautomer, a stereoisomer or a mixture of stereoisomers in any proportions thereof, wherein:

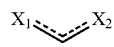

represents

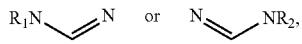

and $R_1$, $R_2$, $R_3$, $R_4$, $R_5$ and $R_6$ are such as defined in claim 1, by reacting an acid addition salt, to the exclusion of a hydriodic acid salt, of a compound of the formula (III) such as defined in claim 7, with bromine, and then with 2 to 7, molar equivalents, in relation to the compound of the formula (III), of a cysteine derivative of the formula (IV) such as defined in claim 7.

14. The method of claim 13, wherein bromine is used in a ratio of 1 to 1.5 molar equivalents in relation to the compound of the formula (III).

15. The method of claim 1 wherein $R_1$ and $R_2$ each represent a hydrogen atom.

16. The method of claim 1 wherein $R_5$ represents a hydrogen atom or a —$COCH_3$ group.

17. The method of claim 1 wherein $R_5$ represents a hydrogen atom.

18. The method of claim 1 wherein $R_6$ represents a hydrogen atom.

19. The method of claim 1, wherein the thiol is soluble in the reaction solvent.

20. The method of claim 1, wherein the solvent used in step (i) is water.

21. The method of claim 2, wherein R represents a linear alkyl chain comprising from 2 to 6 carbons atoms.

22. The method of claim 2, wherein the thiol is 3-mercaptopropionic acid.

23. The method of claim 1, wherein the step (i) is carried out at a temperature between 80° C. and 100° C.

24. The method of claim 1, wherein the compound of the formula (I) represents L-2-thiohistidine.

25. The method of claim 7, wherein the cysteine derivative is cysteine.

26. The method of claim 25, wherein the cysteine derivative is L-cysteine.

27. The method of claim 7, wherein the cysteine derivative of the formula (IV) is used in a ratio of 3 to 5 molar equivalents of the cysteine derivative in relation to the compound of the formula (III).

28. The method of claim 13, wherein 3 to 5 molar equivalents, in relation to the compound of the formula (III), of a cysteine derivative of the formula (IV) such as defined in claim 7 are used.

29. The method of claim 28, wherein the cysteine derivative is cysteine.

30. The method of claim 29, wherein the cysteine derivative is L-cysteine.

* * * * *